United States Patent
Jia et al.

(10) Patent No.: US 11,944,382 B2
(45) Date of Patent: Apr. 2, 2024

(54) SYSTEMS AND METHODS FOR BULK MOTION COMPENSATION IN PHASE-BASED FUNCTIONAL OPTICAL COHERENCE TOMOGRAPGY

(71) Applicant: Oregon Health & Science University, Portland, OR (US)

(72) Inventors: Yali Jia, Portland, OR (US); Xiang Wei, Portland, OR (US)

(73) Assignee: OREGON HEALTH & SCIENCE UNIVERSITY, Portland, OR (US)

(*) Notice: Subject to any disclaimer, the term of this patent is extended or adjusted under 35 U.S.C. 154(b) by 694 days.

(21) Appl. No.: 17/044,559

(22) PCT Filed: Apr. 2, 2019

(86) PCT No.: PCT/US2019/025446
§ 371 (c)(1),
(2) Date: Oct. 1, 2020

(87) PCT Pub. No.: WO2019/195335
PCT Pub. Date: Oct. 10, 2019

(65) Prior Publication Data
US 2021/0093188 A1    Apr. 1, 2021

Related U.S. Application Data

(60) Provisional application No. 62/651,674, filed on Apr. 2, 2018.

(51) Int. Cl.
A61B 3/10  (2006.01)
A61B 3/00  (2006.01)
A61B 5/00  (2006.01)

(52) U.S. Cl.
CPC ............ A61B 3/102 (2013.01); A61B 3/0025 (2013.01); A61B 5/0066 (2013.01)

(58) Field of Classification Search
CPC ...... A61B 3/102; A61B 3/0025; A61B 5/0066
(Continued)

(56) References Cited

U.S. PATENT DOCUMENTS

| 2005/0171438 A1 | 8/2005 | Chen et al. |
| 2008/0025570 A1 | 1/2008 | Fingler et al. |

(Continued)

FOREIGN PATENT DOCUMENTS

| CN | 104523233 A | 4/2015 |
| EP | 2884223 A1 | 6/2015 |

(Continued)

OTHER PUBLICATIONS

International Search Report and Written Opinion from PCT/US2019/025446 dated Jul. 25, 2019, 10 pages.

(Continued)

*Primary Examiner* — Michael A Lyons
*Assistant Examiner* — Omar H Nixon
(74) *Attorney, Agent, or Firm* — Schwabe, Williamson & Wyatt, P.C.

(57) ABSTRACT

Disclosed are methods and systems correcting bulk-motion artifacts in phase-based functional OCT images. The disclosed methods and systems are based on the use of the standard deviation of the phase shift signal present in phase-based OCT imaging. When applied with functional OCT techniques such as OCT angiography, Doppler OCT, and OCT elastography, the disclosed methods provide improved image quality and decreased computational cost compared to other methods of bulk motion compensation.

22 Claims, 9 Drawing Sheets

(58) Field of Classification Search
USPC .......................................................... 356/479
See application file for complete search history.

(56) References Cited

U.S. PATENT DOCUMENTS

| | | |
|---|---|---|
| 2014/0078512 A1 | 3/2014 | Kang et al. |
| 2014/0160484 A1 | 6/2014 | Kang et al. |
| 2014/0221827 A1* | 8/2014 | Motaghiannezam ........................ A61B 5/1128 356/479 |
| 2015/0159992 A1 | 6/2015 | Buckland et al. |
| 2016/0206195 A1* | 7/2016 | Huang .................. A61B 3/1233 |
| 2016/0317027 A1* | 11/2016 | Goto ...................... A61B 3/102 |
| 2017/0164825 A1 | 6/2017 | Chen et al. |

FOREIGN PATENT DOCUMENTS

| | | |
|---|---|---|
| JP | 200803951 A1 * | 2/2008 |
| JP | 2013140077 A | 7/2013 |
| JP | 2016202900 A | 12/2016 |
| WO | 2017-1377567 | 8/2017 |

OTHER PUBLICATIONS

China National Intellectual Property Administration, English translation of the Notification of the First Office Action in counterpart CN Application No. 201980036541.0, dated Dec. 26, 2023, 7 pages.

* cited by examiner

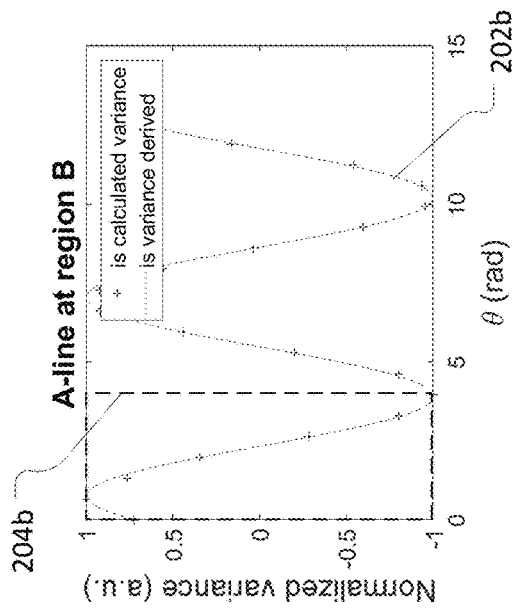
Figure 2A
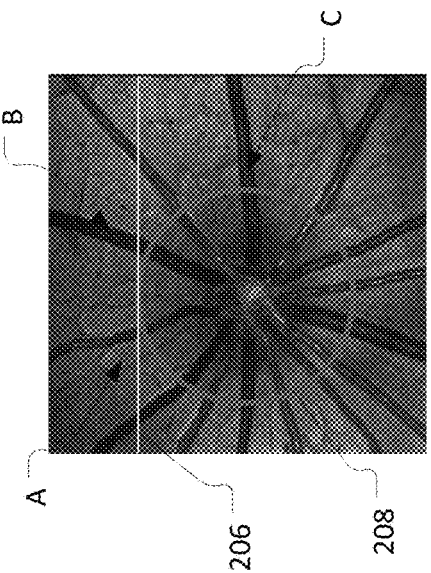
Figure 2B
Figure 2C
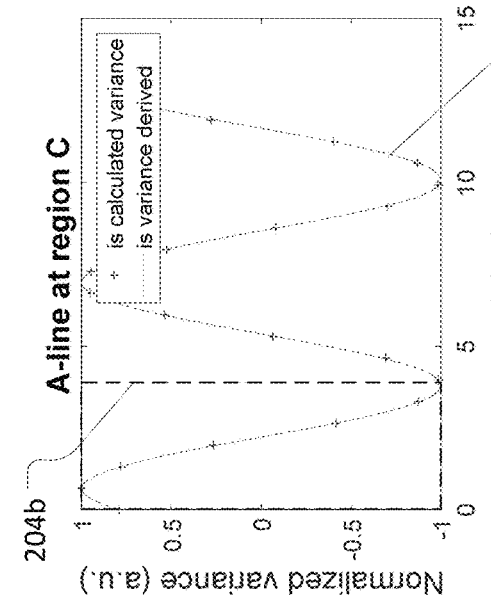
Figure 2D

SYSTEMS AND METHODS FOR BULK MOTION COMPENSATION IN PHASE-BASED FUNCTIONAL OPTICAL COHERENCE TOMOGRAPGY

CROSS REFERENCE TO RELATED APPLICATIONS

The application is a 371 U.S. national stage application which claims priority to PCT/US2019/025446 filed Apr. 2, 2019, which claims priority to U.S. Provisional Application No. 62/651,674, which was filed on Apr. 2, 2018, and titled "SYSTEMS AND METHODS FOR BULK MOTION COMPENSATION IN PHASE-BASED FUNCTIONAL OPTICAL COHERENCE TOMOGRAPHY", the entire disclosures of which are hereby incorporated by reference.

ACKNOWLEDGEMENT OF GOVERNMENT SUPPORT

This invention was made with government support under R01 EY027833, R01 EY024544, and DP3 DK104397 awarded by the National Institutes of Health. The government has certain rights in the invention.

FIELD

Generally, the field involves methods of imaging using optical coherence tomography. In particular, the field involves methods of bulk motion compensation in phase-based functional optical coherence tomography.

BACKGROUND

Optical Coherence tomography (OCT) is a 3-dimensional (3D) imaging technique used to image biological tissues with micrometer resolution. With the advent of Fourier Domain OCT, the increased speed and sensitivity of this technology has enabled new functional capabilities, such as flow imaging by Doppler OCT and OCT angiography (OCTA). Doppler OCT detects the phase shift between adjacent A-scans to provide flow velocity along the axial direction within the macrovasculature. More recently, OCTA was developed to extract intrinsic blood flow signal within the microvasculature by subtracting the OCT signal of adjacent B-scans acquired at the same position. OCTA algorithms based on amplitude or phase signals have been successfully adopted by commercial systems and are routinely used by clinicians for ocular imaging.

However, one major challenge for phase-based functional OCT (e.g., phase-resolved Doppler OCT, phase-based OCTA) is the additional phase shift (difference) caused by bulk motion (e.g., induced by breathing, heartbeats and other involuntary motion). Phase-based methods are more vulnerable to bulk-motion artifacts than amplitude-based methods, so the step to remove bulk-motion phase shift is essential for accurately detecting the flow signal.

Two phase compensation methods have been previously reported and widely used. One is the "average" method, which estimates bulk-motion phase shift by averaging the phase shift along each A-line in the B-frame within the retinal tissue slab. This method may introduce a large error when vessels and their shadows occupy a relative large portion of tissue. The other is the "histogram" method, which estimates this artifact by finding the phase shift with the highest bin number (peak density) in the histogram of all values crossing the tissue on each A-line. The "histogram" method can be more accurate than the "average" method by iteratively subtracting estimated bulk-motion phase shift on each A-line. However, it requires a large computational budget. Thus, there remains a need for a fast and robust method for bulk motion compensation in phase-based functional OCT.

BRIEF DESCRIPTION OF THE SEVERAL VIEWS OF THE DRAWINGS

FIGS. 2A-2D show the suitability of the disclosed methods in fitting OCT imaging data obtained in vivo from a rat eye. FIGS. 2A-2C are the plots of v vs θ at different points. The data in FIG. 2A is from an A-line at a location that contains capillaries only, while the data in FIG. 2B and FIG. 2C are from locations that contain large vessels. FIG. 2D shows the en face OCT mean projection of a scan on a rat eye. Positions labelled A, B, and C in FIG. 2D correspond to respective FIGS. 2A-C.

FIG. 3A depicts the phase difference image before bulk motion compensation. FIG. 3B depicts the phase difference image after bulk motion compensation with the "standard deviation" (STD) method. FIG. 3C illustrates the phase-based OCTA image without bulk motion compensation. FIG. 3D depicts the phase-based OCTA image after bulk motion compensation with STD. FIG. 3E depicts the Doppler OCT image before bulk motion compensation. FIG. 3F depicts the Doppler OCT image after bulk motion compensation with STD method.

FIG. 4A depicts a flow signal calculated without bulk motion compensation (labeled NONE). FIG. 4B depicts a flow signal calculated using "average" (AVG) method. FIG. 4C depicts a flow signal compensated using "histogram" (HIST) method. FIG. 4D depicts a flow signal compensated using "standard deviation" (STD) method. The white arrows indicate where a motion artifact in some place can be suppressed by AVG and STD methods (FIGS. 4B and 4D) and also can be mistakenly enhanced by HIST method (FIG. 4C).

DETAILED DESCRIPTION

Figure 1A:
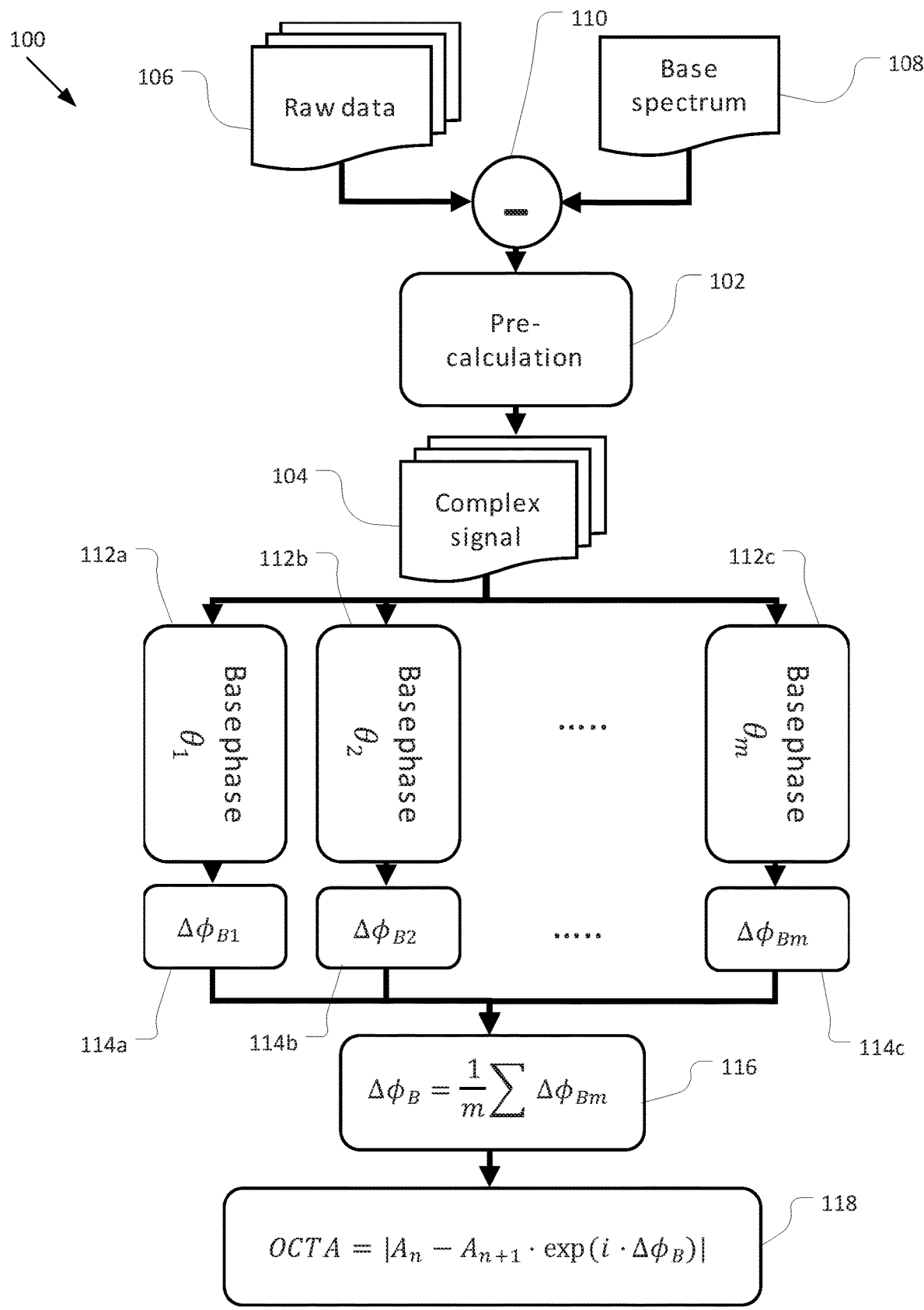
FIG. 1A is a flowchart showing an exemplary procedure to compensate for bulk motion phase shift on phase-based OCTA, in accordance with various embodiments.

Disclosed are methods and systems for removing bulk motion artifacts in OCT applications. In embodiments, the disclosed methods and systems are based on the use of the standard deviation of the phase shift signal present in phase-based OCT imaging.

The disclosed systems and methods are applicable to complex-valued signals, such as OCT signals having both amplitude and phase information. In some embodiments, the disclosed methods and systems are applicable to phase-based functional OCT imaging applications. Examples of functional OCT imaging include retinal Doppler OCT, OCT angiography (OCTA), and OCT elastography.

An aspect of the disclosed methods and systems is that they provide robust and computationally efficient approaches for bulk motion compensation in phase-based functional OCT imaging. Compared to other bulk-motion compensation methods known in the art, the disclosed methods provide improvements in image quality with reduced processing time.

Also disclosed herein is an exemplary system for acquiring and performing bulk-motion compensation using the disclosed methods. The exemplary system comprises an OCT device configured to acquire OCT structural and angiography data in functional connection with a computing device having a logic subsystem and data holding capabilities. In embodiments the computing device is configured to receive data from the OCT device and perform one or more operations of the methods described herein.

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth (z-direction).

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value, a complex value having both amplitude and phase information, a decorrelation value, or other signal representations). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset reflecting flow within the imaged sample. There is a correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a 2D projection of the three dimensional dataset onto a single planar image called an en face angiogram. Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer could be used to generate an en face angiogram of the inner retina). Once generated, the en face angiogram image may be used to quantify various features of the retinal vasculature as described herein. This quantification typically involves the setting of a threshold value to differentiate, for example, the pixels that represent flow within vasculature from static tissue within the angiogram. These en face angiograms can be interpreted in a manner similar to traditional angiography techniques such as fluorescein angiography (FA) or indocyanine green (ICG) angiography, and are thus well-suited for clinical use. It is also common to generate en face images from structural OCT data in a manner analogous to that used to generate en face angiograms. Angiograms from different layers may also be color-coded and overlaid to present composite angiograms with encoded depth information; structural en face images may also be included in such composite image generation.

Functional OCT, as used herein, broadly refers to the extension of OCT techniques to provide information beyond structural characterization. For example, whereas structural OCT imaging may be used to gather spatial information about a tissue's anatomical organization, functional OCT may be used to gather information about processes occurring within that tissue sample such as blood flow, tissue perfusion and oxygenation, birefringence, etc. Examples of functional OCT include, but are not limited to, OCT angiography (OCTA) and associated techniques for characterizing blood flow, Doppler OCT, polarization-sensitive OCT, OCT elastography, spectroscopic OCT, differential absorption OCT, and molecular imaging OCT.

Disclosed herein are methods and systems to compensate for bulk-motion artifacts in phase-based optical coherence tomography (OCT). Phase-based OCT applications, such as OCT angiography (OCTA), Doppler OCT, and OCT elastography, are sensitive to the confounding phase shift introduced by subject bulk motion. Traditional bulk motion compensation methods are limited by their accuracy and computing cost-effectiveness. The novel bulk motion compensation method for phase-based functional OCT described herein offers advantages over traditional methods both in terms of improved image quality and decreased computational burden.

Disclosed herein is a novel method of bulk motion compensation based on the standard deviation of OCT flow signals. An explicit equation of the bulk motion can be derived and subtracted from phase-based functional OCT. An aspect of the disclosed bulk motion compensation method is that it is more effective than previous averaging and histogram-based methods for reducing motion artifacts in OCT datasets. In addition, the method is less computationally intensive than these previous methods.

The OCT complex signal (amplitude and phase) at one specific lateral location, axial location z, and time t can be described as:

$$B_{oct}(t,z) = A(t,z) \exp[i\phi(t,z)] \qquad \text{Eq. (1)}$$

where $B_{oct}(t, z)$ is a complex signal, $A(t, z)$ is the amplitude and $\phi$ is the phase. The phase term includes three components and can be expanded as:

$$\phi(t,z) = \phi_P(t,z) + \phi_B(t,z) + \phi_M(t,z) \qquad \text{Eq. (2)}$$

where $\phi_P(t,z)$ is the phase shift caused by the moving red blood cell inside vessels, $\phi_B(t, z)$ is the phase shift caused by the bulk motion, and $\phi_M(t, z)$ is the phase shift caused by the system's modulation frequency. The absolute value of the difference between two repeated B-scans can be expressed as:

$$B_{diff} = \{A^2(t_1,z) + A^2(t_2,z) - 2A(t_1,z)A(t_2,z)\cos[\Delta\phi_P + \Delta\phi_B]\}^{1/2} \qquad \text{Eq. (3)}$$

Here, the time coordinate of the second scan can be represented as $t_2 = t_1 + \Delta t$. The system modulation phase difference is assumed to be a constant for all A-scans and can be removed. The term of $\Delta\phi_B$ can be expressed in the standard deviation analysis of $B_{diff}$:

$$s = \sqrt{\langle B_{diff}^2 \rangle - (\langle B_{diff} \rangle)^2} \qquad \text{Eq. (4)}$$

Plugging Eq. (3) into Eq. (4) yields:

$$s = \sqrt{C_1 - C_2 \cos(\Delta\phi_B)} \qquad \text{Eq. (5)}$$

where $C_1$ and $C_2$ are constants. The phase shift contribution from the vessels is relatively small compared to that of the tissue, so $\Delta\phi_P$ may be ignored in this calculation. Accordingly, the variance v is expressed as:

$$v = s^2 = C_1 - C_2 \cos(\Delta\phi_B) \qquad \text{Eq. (6)}$$

Based on the explicit bulk motion equation, one can directly solve the bulk motion phase. In order to solve this equation, an artificial subtraction of a phase θ to the complex signal $B_{oct}(t+\Delta t, z)$ is performed:

$$B'_{oct}(t+\Delta t, z) = B_{oct}(t+\Delta t, z) \cdot \exp(-i\theta) \qquad \text{Eq. (7)}$$

The variance may then be expressed as:

$$v = C_1 - C_2 \cos(\Delta\phi_B + \theta) \qquad \text{Eq. (8)}$$

The variance is a cosine function having phase θ. The bulk motion phase $\Delta\phi_B$ can be directly solved at variance values at four phase values θ spaced at π/2 interval. For example, in embodiments, phase values of θ=0, π/2, π, 3π/2, can be chosen to initiate the computation:

$$v_1 = std(|A_n - A_{n+1}|)^2 \qquad \text{Eq. (10)}$$

$$v_2 = std(|A_n - A_{n+1} \cdot \exp(-i \cdot \pi)|)^2 \qquad \text{Eq. (11)}$$

$$v_3 = std\left(\left|A_n - A_{n+1} \cdot \exp\left(-i \cdot \frac{\pi}{2}\right)\right|\right)^2 \qquad \text{Eq. (12)}$$

$$v_4 = std\left(\left|A_n - A_{n+1} \cdot \exp\left(-i \cdot \frac{3\pi}{2}\right)\right|\right)^2 \qquad \text{Eq. (13)}$$

Here, $A_n$ is the $n^{th}$ repeated A-line from the $n^{th}$ consecutive B-frames at the same location. Then the bulk motion phase shift can be written as, $$\Delta\phi_B = \text{atan2}\left(\frac{v_3 - v_4}{v_2 - v_1}\right) \qquad \text{Eq. (14)}$$

where the atan2 is the four-quadrant inverse tangent. Thus, based on Eq. (14), directly the bulk motion phase shift can be solved for.

In embodiments, the calculation accuracy of Eq. (14) can be increased by solving the equation multiple times by shifting the four sampling point values. For example, in order to increase the calculation accuracy of calculation in the examples provided below, Eq. (14) may be solved five times by shifting the four sampling points together with a random base phase $\theta_m$ (i.e., at $\theta_m$, $\theta_m + \pi/2$, $\theta_m + \pi$ and $\theta_m + 3\pi/2$). Five $\Delta\phi_{Bm}$ may be calculated and averaged to obtain the final bulk motion phase shift $\Delta\phi_B$ for each A-line. Other embodiments may use any suitable number of $\Delta\phi_{Bm}$ values averaged together.

Figure 1B:
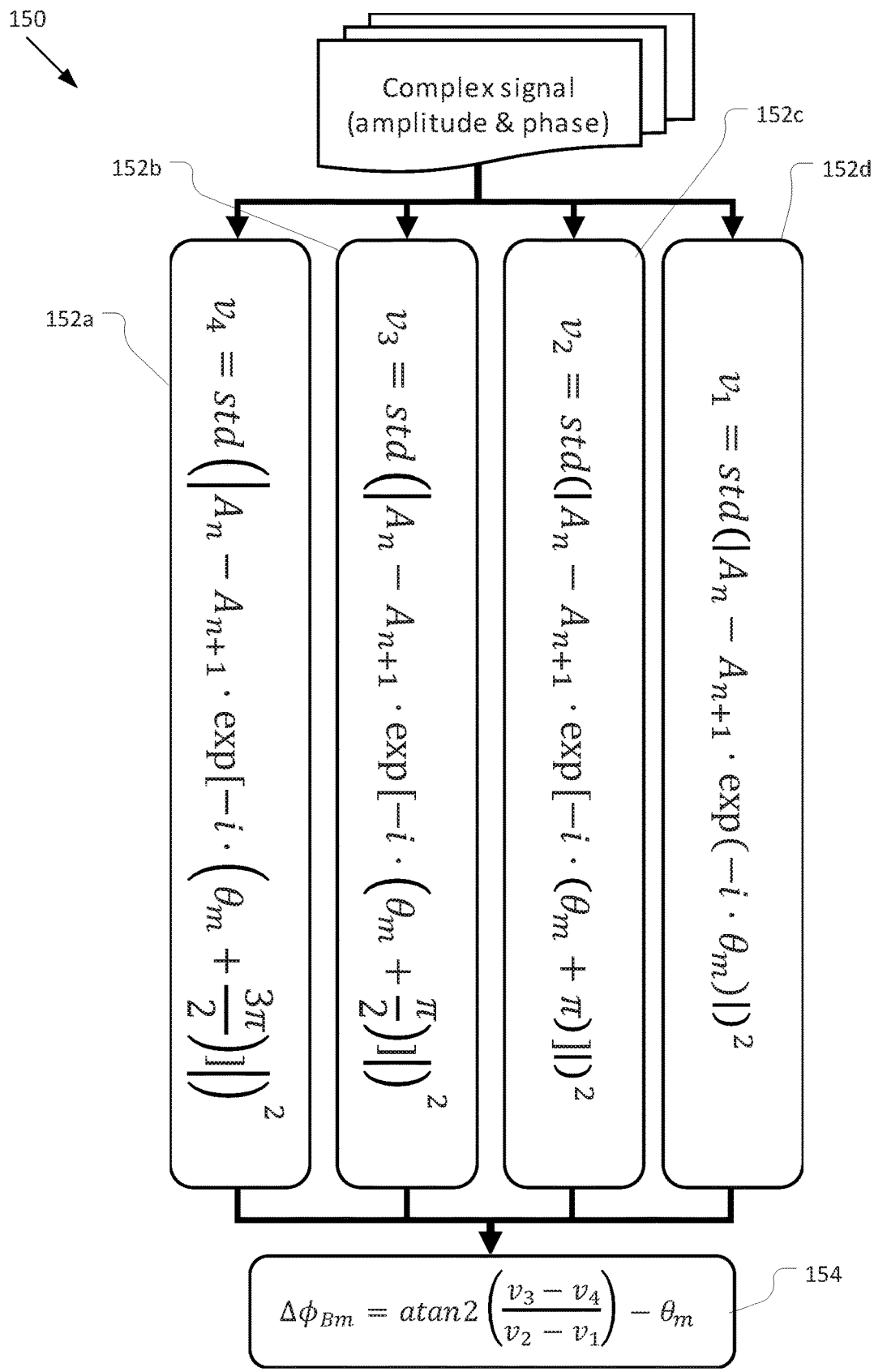
FIG. 1B is a flowchart showing the estimation of bulk motion phase shift $\Delta\phi_{Bm}$ on base phase $\theta_m$, in accordance with various embodiments.

A flowchart illustrating a method 100 for bulk-motion compensation is shown in FIGS. 1A and 1B, in accordance with various embodiments described herein. In embodiments, the method 100 may be applied to OCTA scans. In some embodiments, the method 100 may include a pre-calculation operation, as shown at 102 in FIG. 1A. This pre-calculation operation 102 may include, for example, one or more signal processing operations to extract complex OCT signal data 104 from raw OCT spectrum data 106 (e.g., raw OCT spectrum data 106 subtracted by base spectrum 108 as shown at 110 of method 100). Such signal processing operations may include, but are not limited to, one or more operations for dispersion compensation, conversion from wavelength to frequency representation, wave number interpolation, and/or Fast Fourier Transform operations.

In embodiments, bulk motion may then be estimated from complex OCT signal data 104 using a "standard deviation" method as described herein. For example, as described above, one or more base phases (e.g., $\theta_1, \theta_2, \ldots \theta_m$) may be selected at 112a-c of the method 100. The one or more base phases may be randomly selected, semi-randomly selected, or may be predetermined phase values. The phase difference $\Delta\phi_{Bm}$ due to bulk motion may be determined for each base phase at 114a-c of the method 100.

FIG. 1B illustrates a method 150 of determining the phase difference $\Delta\phi_{Bm}$ for a single base phase in more detail. For example, the method 150 includes determining the variance values at four phase values spaced at $\pi/2$ interval relative to the base phase according to Equations (10)-(13) (noted as operations 152a-d in FIG. 1B). The bulk motion phase difference $\Delta\phi_{Bm}$ for the given base phase is then determined at 154 of method 150 (e.g., according to Equation (14)).

Referring again to FIG. 1A, the bulk motion phase differences $\Delta\phi_{Bm}$ for the multiple base phases may be averaged at 116 of method 100, to obtain a bulk motion phase shift $\Delta\phi_B$ for each A-line. The averaging operation at 116 may be omitted when a single set of variance values at one base phase is used. At 118 of the method 100, individual A-lines of the OCT dataset may be adjusted based on the bulk motion phase shift $\Delta\phi_B$ to obtain a bulk-motion compensated OCT dataset.

EXAMPLES

The following examples are illustrative of the disclosed methods. In light of this disclosure, those skilled in the art will recognize that variations of these examples and other examples of the disclosed method would be possible without undue experimentation.

Example 1

Accuracy of the "Standard Deviation" Method

The accuracy of the proposed method relies, in part, on how experimental results correlate with the cosine curve representation as predicted by Eq. (8). In other words, for results to be well-fit, it is necessary to retrieve an accurate bulk motion phase shift at the first lowest value of cosine function. To verify this was the case with experimental data, a single A-scan was randomly chosen from three different locations (one location in static tissue with capillaries only, and two locations in large vessels) within an OCT dataset of an in vivo rat eye. The relationship between the variances calculated at various $\theta$ from data and the variance derived directly from Eq. (8) was investigated.

FIGS. 2A-2C show plots of v vs $\theta$ at three different points within the rat eye (denoted as region A, B, and C in FIG. 2D). The '+' marks on the plots are the calculated variances, normalized to −1 to 1. The curve 202a-c is the cosine function derived from the Eq. 8, the region 204a-c on the left side of each graph indicates the phase shift caused by bulk motion. In FIG. 2A, the A-line chosen from a point that contains capillaries only, while FIGS. 2B and 2C have A-lines chosen from points that contain large vessels. FIG. 2D shows an en face OCT mean projection of a scan of a rat eye. Labelled position A, B, and C within FIG. 2D correspond to plots of FIGS. 2A, 2B, and 2C. The high quality of the curve fits in FIGS. 2A, 2B, and 2C suggests that Eq. (8) is correct and that the bulk motion phase shift can be directly solved using Eq. (14).

Example 2

Application in Rodent Eyes

Retinal Doppler OCT and OCTA scans were acquired on rats to validate the disclosed systems and methods for bulk motion compensation. The performance of the bulk motion compensation systems and methods, including image quality and computational needs, was evaluated. An exemplary prototype visible-light spectral-domain OCT system was used for imaging rodents. The system had a 50-kHz scanning rate, center wavelength at 560 nm and axial resolution of 1.53 µm. All the experimental procedures were approved by the Institutional Animal Care and Use Committee (IACUC).

FIGS. 3A-3F show representative data for an in vivo rat imaging experiment demonstrating the effectiveness of the disclosed methods for both OCTA and Doppler OCT applications. Cross-sectional OCT images were acquired from the same volumetric scan as shown in FIG. 2D. An OCTA image was acquired at the position indicated by the horizontal line 206 in FIG. 2D. A Doppler OCT image was acquired from the circular scan indicated by the circle 208 in FIG. 2D.

Figure 3A:
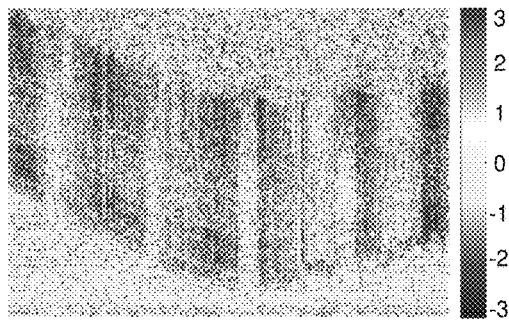
FIGS. 3A-3F depicting cross section data in a rat eye and illustrate the image improvement afforded by the disclosed methods.
Figure 3B:
Figure 3C:
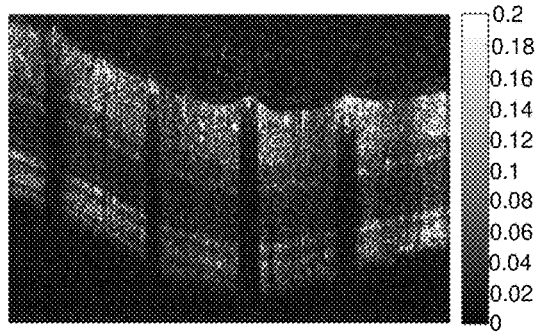
Figure 3D:
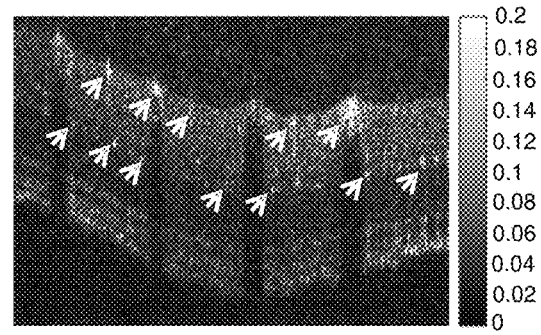
Figure 3E:
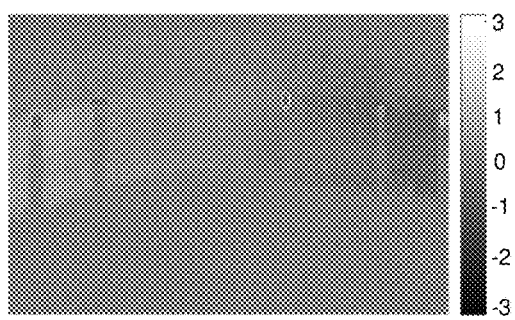
Figure 3F:
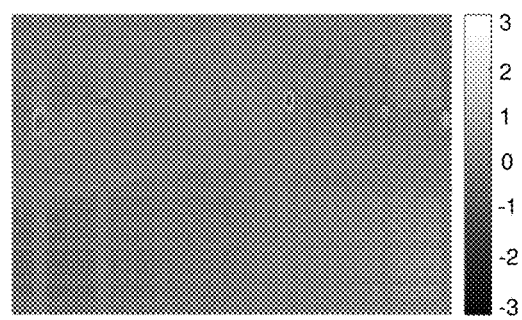

FIG. 3A shows the phase difference image before bulk motion compensation, wherein the colored fringes indicate the bulk motion phase shift. FIG. 3B shows the phase difference image after bulk motion compensation with the "standard deviation" (STD) method. FIG. 3C shows the phase-based OCTA image without bulk motion compensation, where retinal flow signals are indistinguishable from motion artifact. FIG. 3D shows the phase-based OCTA image after bulk motion compensation using the disclosed STD method, where true flow signals (indicated by yellow arrows) are rendered distinguishable. FIG. 3E shows a Doppler OCT image before bulk motion compensation, where a large amount of motion signal and low Doppler signal contrast is present. FIG. 3F shows the Doppler OCT image after bulk motion compensation with STD method, where Doppler signal contrast is improved. The range of color bars in FIGS. 3A, 3B, 3E, and 3F is the phase from $-\pi$ to $\pi$. The range of color bars in FIGS. 3C and 3D is the normalized amplitude from 0 to 0.2.

The disclosed "standard deviation" method was also qualitatively and quantitatively evaluated on en face angiograms by comparing to two conventional methods—"average" and "histogram" methods—on the same dataset from a rat eye. To ensure a valid comparison between the three bulk-motion removal methods, all data were processed using the same operations with the exception of the phase compensation technique that was used.

Figure 4A:
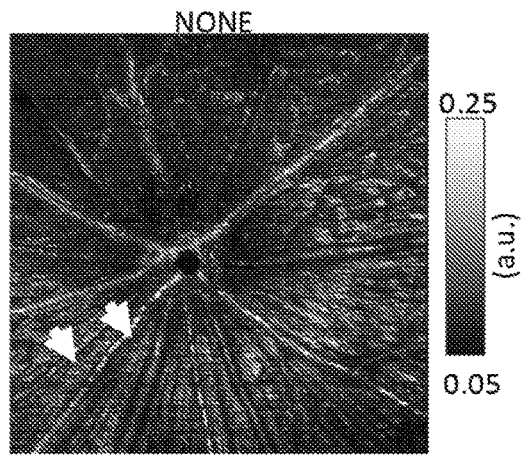
FIGS. 4A-4D are images showing a comparison of different bulk motion compensation methods applied to a rat eye.
Figure 4B:
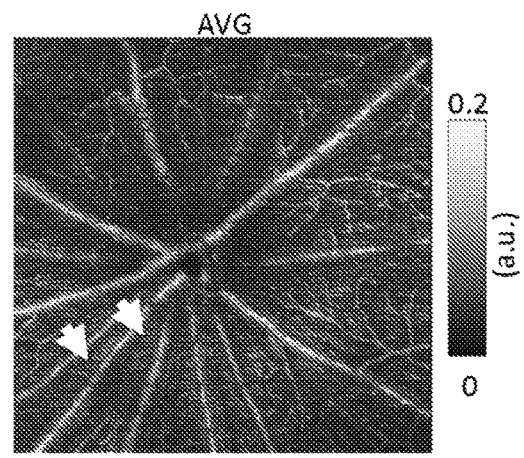
Figure 4C:
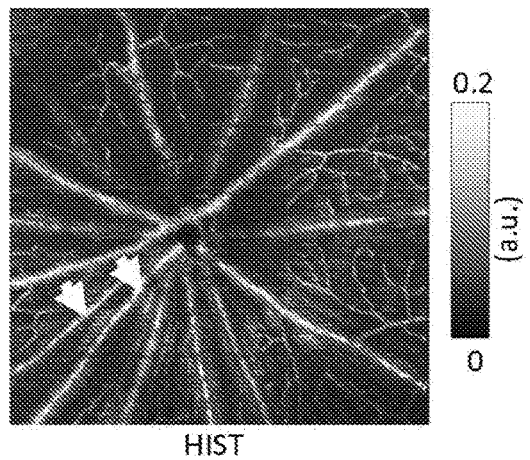
Figure 4D:
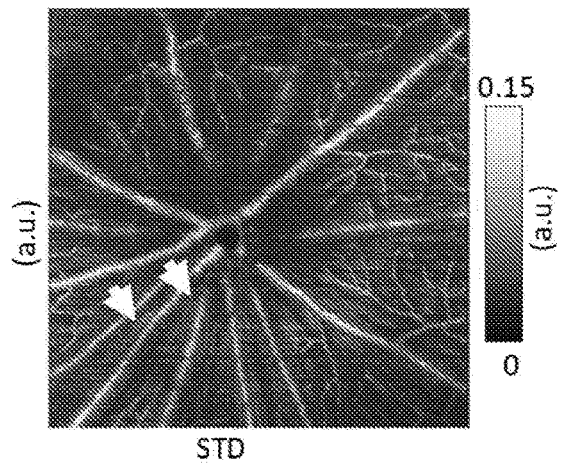
Figures 5A, 5B, 5C:
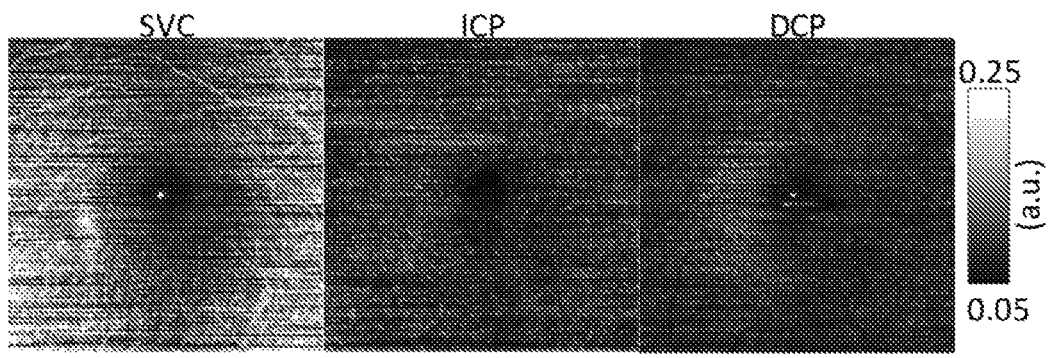
FIGS. 5A-5L are images showing a comparison of different bulk motion compensation methods applied at different depths within a human retina.
Figures 5D, 5E, 5F:
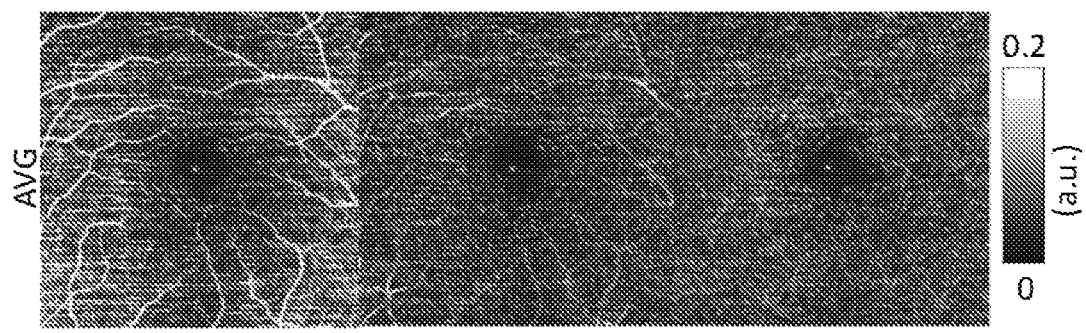
Figures 5G, 5H, 5I:
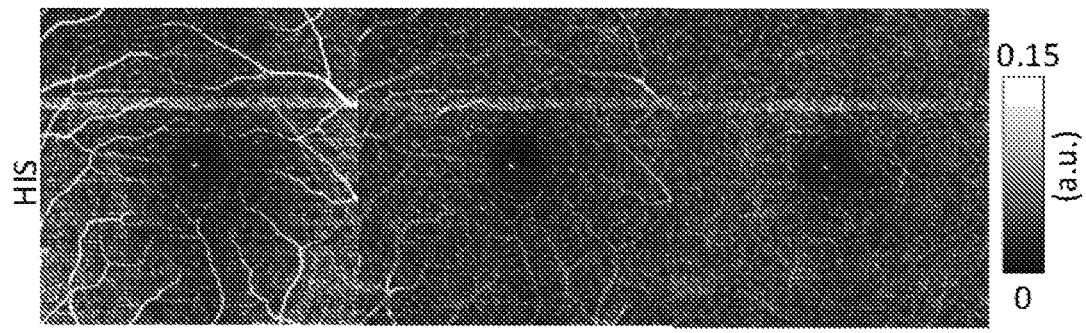
Figures 5J, 5K, 5L:
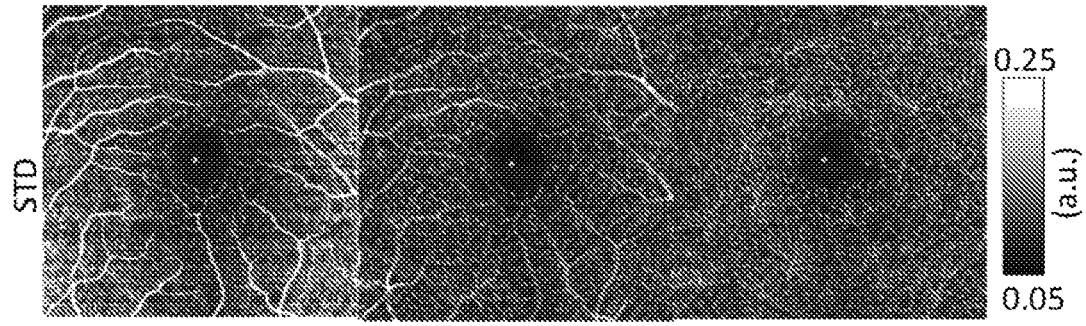

Compared to OCTA without compensation step (FIG. 4A), the image compensated by the "average" method (FIG. 4B) reveals some microvascular details, but retains high background noise (bulk motion artifacts). The "histogram" method (FIG. 4C) suppressed artifacts and improved image contrast, but there were errors introduced by the compensation step (denoted by white arrows). Overall, the image processed by the "standard deviation" method (FIG. 4D) showed the best image quality for rodent retinal imaging.

Example 3

Application in Human Eyes

Retinal Doppler OCT and OCTA scans were acquired on humans to validate the disclosed systems and methods for bulk motion compensation. The performance of the bulk motion compensation systems and methods, including image quality and computational needs, was evaluated. A commercial spectral-domain OCT system (RTVue-XR Avanti; Optovue, Inc., Fremont, CA) with 70-kHz scanning rate, center wavelength at 840 nm and an axial resolution of 5 um, was used for imaging the human retina. Written informed consent was obtained from all volunteers. All the experimental procedures were approved by the Institutional Review Board/Ethics Committee of OHSU. Ten human retinal scans, encompassing a 3 mm×3 mm region of the macula, were acquired from 5 volunteers.

The disclosed "standard deviation" bulk-motion removal method was compared to conventional "average" and "histogram" methods by processing the same dataset using each method. Using en face angiograms, both qualitative and quantitative evaluations were made. To ensure a valid comparison between the three bulk-motion removal methods, all data were processed using the same signal processing operations in the workflow with the exception of the phase compensation technique that was used. The superficial vascular complex (SVC), intermediate capillary plexuses (ICP), and deep capillary plexuses (DCP) en face images were generated using custom automatic segmentation software.

FIGS. 5A-5L shows the effect of different bulk motion compensation methods on en face maximum projection of flow in three different slabs (the SVC, ICP, and DCP). The three columns of FIGS. 5A-5L correspond to the three different slabs analyzed. The first column (i.e., FIGS. 5A, 5D, 5G, and 5J) shows the superficial vascular complex (SVC); the second column (i.e., FIGS. 5B, 5E, 5H, and 5K) shows the intermediate capillary plexus (ICP); and the third column (i.e., FIGS. 5C, 5F, 5I, and 5L) shows the deep capillary plexus (DCP). The four rows of FIGS. 5A-5L correspond to the four different bulk motion compensation methods applied. The first row (FIGS. 5A-5C) was calculated without bulk motion compensation (NONE), the second row (FIGS. 5D-5F) was calculated using the "average" (AVG) method, the third row (FIGS. 5G-5L) was calculated using the "histogram" (HIST) method, and the fourth row (FIGS. 5J-5L) was calculated using the "standard deviation" (STD) method. These image quality and level of detail captured using the compared methods supports the ability of the "standard deviation" method to produce superior image quality compared to "average" and "histogram" methods.

Image quality after bulk motion compensation was also investigated by calculating the flow signal to noise ratio (SNR). Since the foveal avascular zone (FAZ) is a known landmark devoid of flow, it is a good noise reference in the healthy retina, and the SNR can be calculated by the ratio of parafoveal flow to the FAZ signal. The ganglion cell layer plexus was the only slab used to analyze SNR, in order to remove the interference of a large amount of residual motion signal within nerve fiber layer. The SNR calculations showed that the "standard deviation" method had a 62% image quality improvement compared to the "average" method while the histogram method had a 22% image quality improvement over the "average" method (Table 1).

TABLE 1

Signal-to-Noise ratio (SNR) of three bulk-motion compensation methods

| Method | AVG | HIST | STD |
|---|---|---|---|
| SNR(mean ± std) | 1.08 ± 0.55 | 1.32 ± 0.40 | 1.75 ± 0.58 |
| Improvement | — | 22% | 62% |

Example 4

Computational Performance

Figure 6:
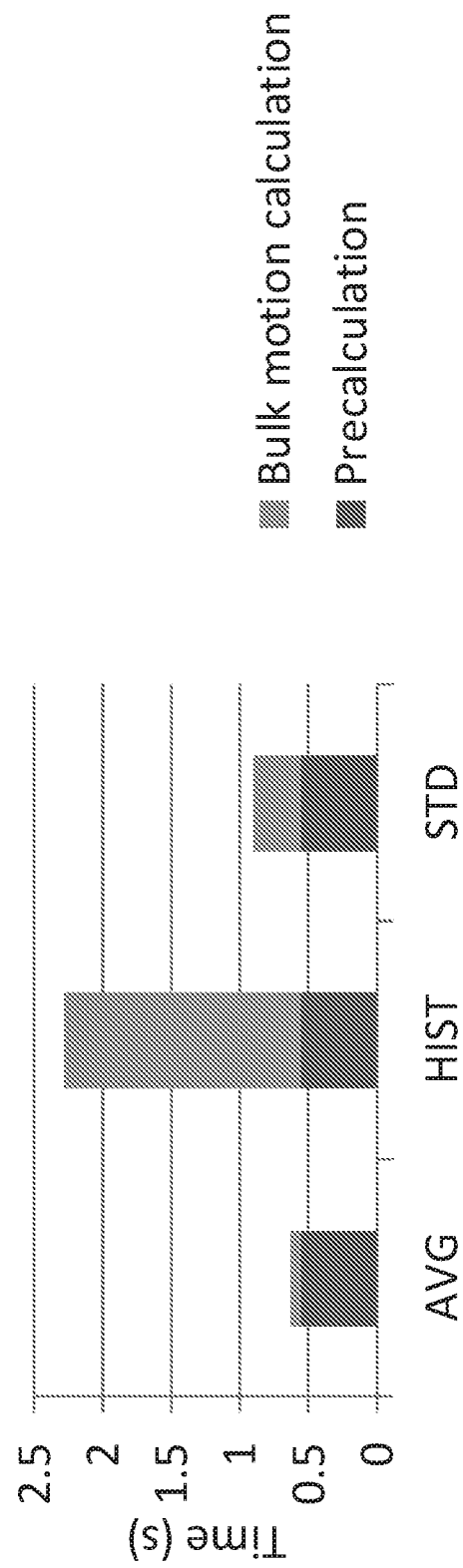
FIG. 6 is a bar graph showing a comparison of the computational budget required for the AVG, HIST, and STD methods.

FIG. 6 is a graph showing the computational performance (or computational budget) of the three bulk motion removal calculations: the "average" method, the "histogram" method, and the disclosed "standard deviation" method. These computing platform used for this comparison was an Intel Core i7 6700k, 32 GB RAM, single processing system with the methods implemented using Matlab 2017a (The Mathworks, Natick, MA). As shown in FIG. 6, the "average" method had the lowest computational budget but also the lowest image quality. The "histogram" method had a higher image quality compared to the "average" method, but due to the required number of iterations, it had the highest computational budget. The "standard deviation" method had a relatively low computational budget as well as the best image quality. The "standard deviation" method for bulk motion calculation was almost 5 times faster than that of the "histogram" method.

Example 5

Calculation Procedure

Figure 9:
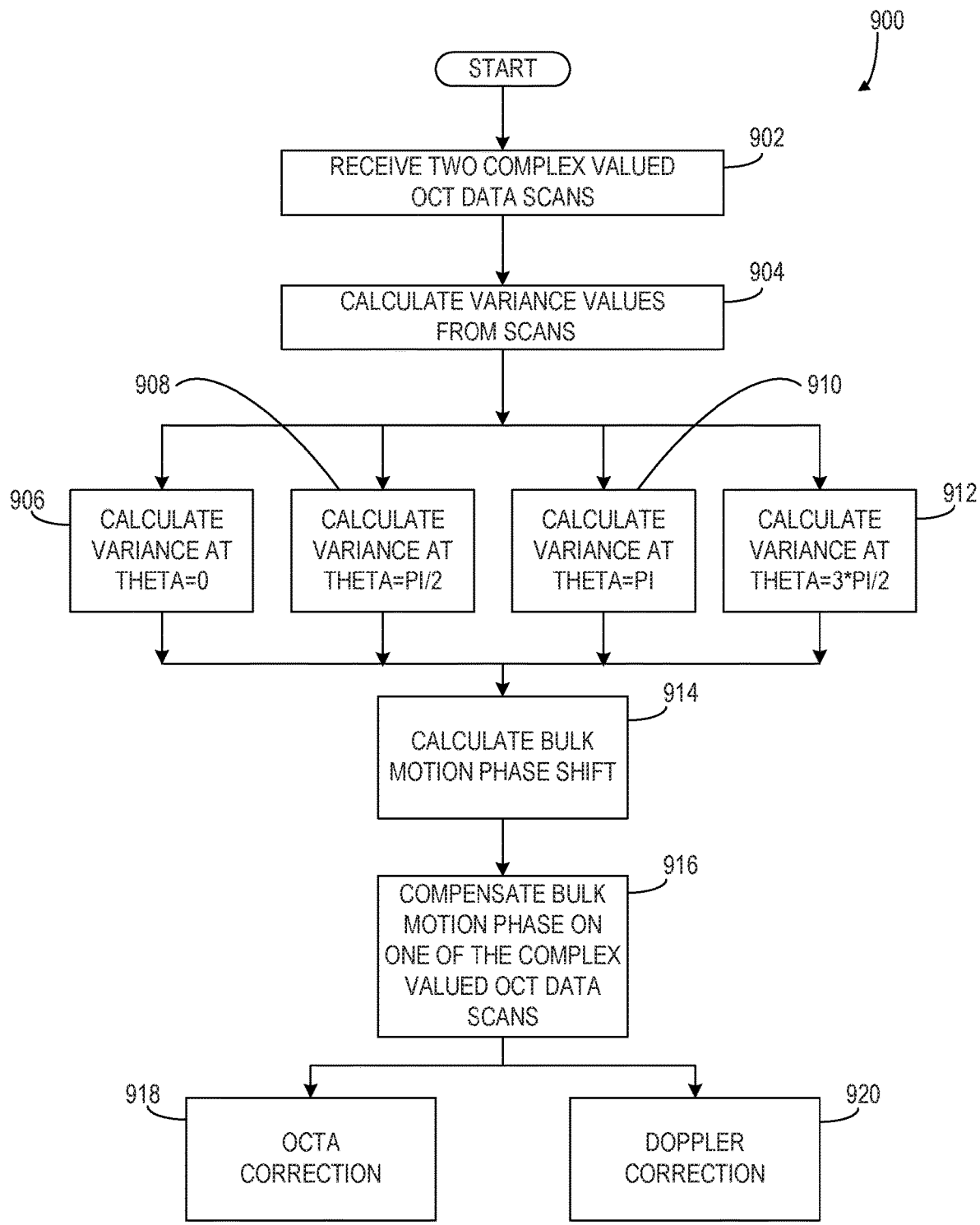
FIG. 9 is a flowchart of a method for calculating bulk motion phase correction for OCT, in accordance with various embodiments.

FIG. 9 shows an exemplary procedure 900 for calculating bulk motion phase correction for OCTA and Doppler applications. Beginning at 902, complex OCT A-scan data $A_n$ and $A_{n+1}$ are received. In the context of OCTA, for example, these two scans $A_n$ and $A_{n+1}$ may be two repeated scans at the same location. In a Doppler imaging context, these two scans may be two adjacent scans which may have some overlap. One of the scans is considered the reference OCT signal while the other scan is the signal having bulk motion that requires correction or compensation. For example, if the reference signal is designated as scan $A_n$, its corresponding signal containing bulk motion that requires compensation is scan $A_{n+1}$.

At 904, the variance values of the signals in scans $A_n$ and $A_{n+1}$ are calculated using the following equation:

$$v=[\text{std}(A_n - A_{n+1} \cdot \exp(-i \cdot \theta))]^2 \quad \text{Eq. (15)}$$

This variance equation, Eq. (15), is next evaluated at four different values of θ. In this particular example, at 906, 908, 910, and 912, θ is evaluated at values of θ=0, π/2, π, 3π, 2, respectively. This yields the following set of variance values:

$$v_1 = \text{std}(|A_n - A_{n+1}|)^2 \quad \text{previous Eq. (10)}$$

$$v_2 = \text{std}(|A_n - A_{n+1} \cdot \exp(-i \cdot \pi)|)^2 \quad \text{previous Eq. (11)}$$

$$v_3 = \text{std}\left(\left|A_n - A_{n+1} \cdot \exp\left(-i \cdot \frac{\pi}{2}\right)\right|\right)^2 \quad \text{previous Eq. (12)}$$

-continued $$v_4 = std\left(\left|A_n - A_{n+1} \cdot \exp\left(-i \cdot \frac{3\pi}{2}\right)\right|\right)^2 \quad \text{previous Eq. (13)}$$

At 914, based on the recognition that the variance has the form described in Eq. (8) above:

$$v = C_1 - C_2 \cos(\Delta\phi_B + \theta) \quad \text{Eq. (8)}$$

The bulk motion phase shift can be calculated using Eq. (14) above:

$$\Delta\phi_B = \text{atan2}\left(\frac{v_3 - v_4}{v_2 - v_1}\right) \quad \text{previous Eq. (14)}$$

This bulk motion phase shift $\Delta\phi_B$ can then be used to compensate for bulk motion phase in the A-scan signal requiring correction. For example, as shown at 916, if the reference signal is designated as scan $A_n$, then the bulk motion phase on corresponding signal scan $A_{n+1}$ can be compensated using:

$$A_{new} = A_{n+1} \cdot \exp(i \cdot \Delta\phi_B) \quad \text{Eq. (16)}$$

Once the $A_{new}$ value is calculated, it may be use to provide correction in OCTA applications at 918 as $$\text{OCTA} = |A_n - A_{new}| \quad \text{Eq. (17)}$$

or in Doppler imaging applications at 920 as:

$$\text{doppler} = \text{angle}(A_n \times \text{conj}(A_{new})) \quad \text{Eq. (18)}$$

Example 6

Optical Coherence Tomography Angiography Image Processing System

Figure 7:
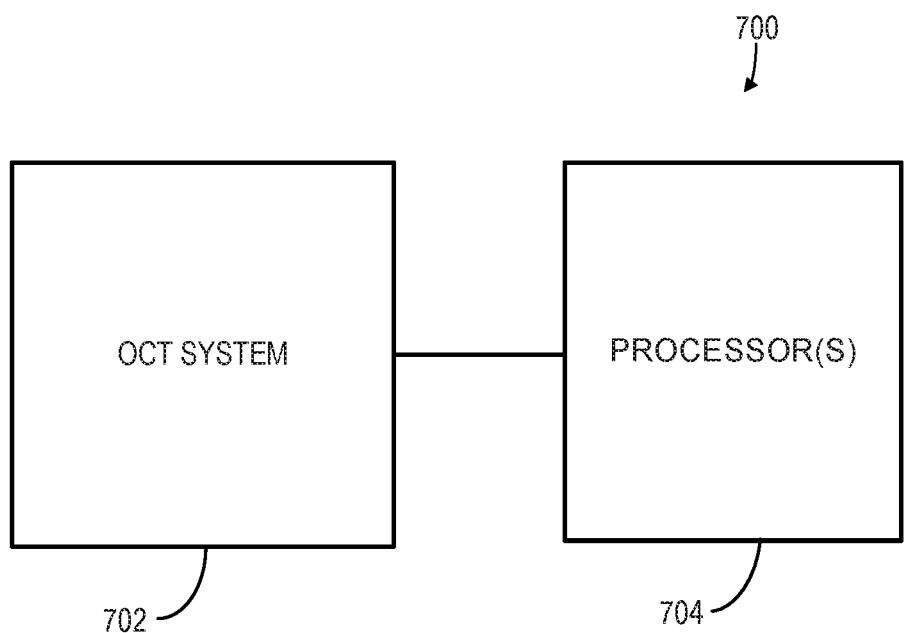
FIG. 7 schematically shows an example system for processing OCT and OCT angiography datasets to detect areas of nonperfusion in accordance with the disclosure.

FIG. 7 schematically shows an example system 700 for OCT image processing in accordance with various embodiments. System 700 comprises an OCT system 702 configured to acquire an OCT image comprising OCT interferograms and one or more processors or computing systems 704 that are configured to implement the various processing routines described herein. OCT system 700 can comprise an OCT system suitable for structural OCT and OCT angiography applications, e.g., a swept source OCT system or spectral domain OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the methods 100 depicted in FIG. 1A and, the method 150 depicted in FIG. 1B, and/or the procedure 900 depicted in FIG. 9, described above, can be implemented as a computer application, computer service, computer API, computer library, and/or other computer program product.

Figure 8:
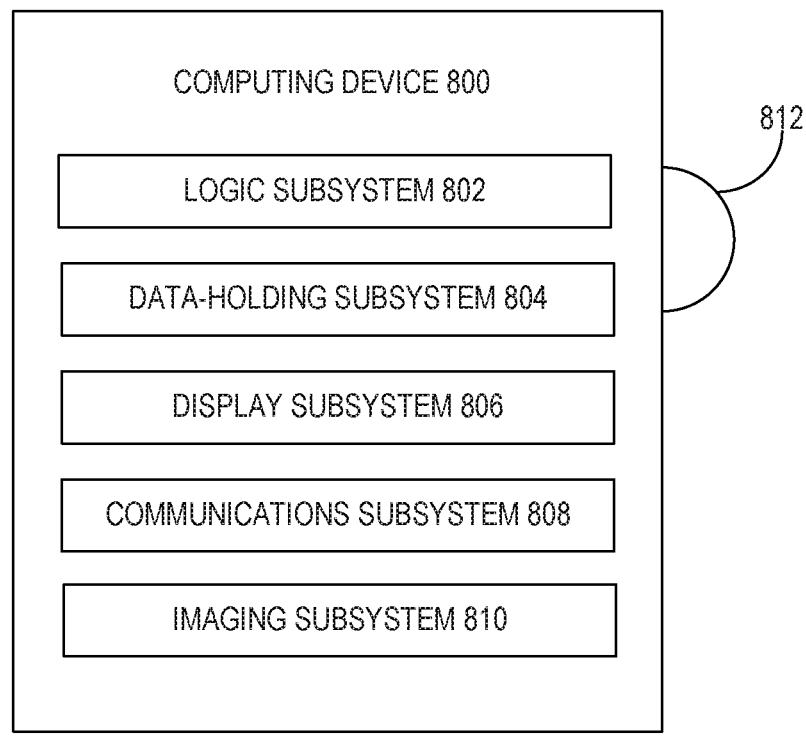
FIG. 8 schematically shows an example of a computing system in accordance with the disclosure.

FIG. 8 schematically shows a non-limiting computing device 800 that can perform one or more of the above described methods and processes. For example, computing device 800 can represent a processor included in system 700 described above, and can be operatively coupled to, in communication with, or included in an OCT system or OCT image acquisition apparatus. Computing device 800 is shown in simplified form. It is to be understood that virtually any computer architecture can be used without departing from the scope of this disclosure. In different embodiments, computing device 800 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 800 includes a logic subsystem 802 and a data-holding subsystem 804. Computing device 800 can optionally include a display subsystem 806, a communication subsystem 808, an imaging subsystem 810, and/or other components not shown in FIG. 8. Computing device 800 can also optionally include user input devices such as manually actuated buttons, switches, keyboards, mice, game controllers, cameras, microphones, and/or touch screens, for example.

Logic subsystem 802 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 804 can include one or more physical, non-transitory, devices configured to hold data and/or instructions executable by the logic subsystem to implement the herein described methods and processes.

When such methods and processes are implemented, the state of data-holding subsystem 804 can be transformed (e.g., to hold different data).

Data-holding subsystem 804 can include removable media and/or built-in devices. Data-holding subsystem 804 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 804 can include devices with one or more of the following characteristics: volatile, nonvolatile, dynamic, static, read/write, read-only, random access, sequential access, location addressable, file addressable, and content addressable. In some embodiments, logic subsystem 802 and data-holding subsystem 804 can be integrated into one or more common devices, such as an application specific integrated circuit or a system on a chip.

FIG. 8 also shows an aspect of the data-holding subsystem in the form of removable computer-readable storage media 812, which can be used to store and/or transfer data and/or instructions executable to implement the herein described methods and processes. Removable computer-readable storage media 812 can take the form of CDs, DVDs, HD-DVDs, Blu-Ray Discs, EEPROMs, flash memory cards, USB storage devices, and/or floppy disks, among others.

When included, display subsystem 806 can be used to present a visual representation of data held by data-holding subsystem 804. As the herein described methods and processes change the data held by the data-holding subsystem, and thus transform the state of the data-holding subsystem, the state of display subsystem 806 can likewise be transformed to visually represent changes in the underlying data. Display subsystem 806 can include one or more display devices utilizing virtually any type of technology. Such display devices can be combined with logic subsystem 802 and/or data-holding subsystem 804 in a shared enclosure, or such display devices can be peripheral display devices.

When included, communication subsystem 808 can be configured to communicatively couple computing device 800 with one or more other computing devices. Communication subsystem 808 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 800 to send and/or receive messages to and/or from other devices via a network such as the Internet.

When included, imaging subsystem 810 can be used acquire and/or process any suitable image data from various sensors or imaging devices in communication with computing device 800. For example, imaging subsystem 810 can be configured to acquire OCT image data, e.g., interferograms, as part of an OCT system, e.g., OCT system 702 described above. Imaging subsystem 810 can be combined with logic subsystem 802 and/or data-holding subsystem 804 in a shared enclosure, or such imaging subsystems can comprise periphery imaging devices. Data received from the imaging subsystem can be held by data-holding subsystem 804 and/or removable computer-readable storage media 812, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of bulk motion compensation of phased-based functional optical coherence tomography (OCT), the method comprising:
    receiving, via an OCT system, a first complex-valued OCT A-scan, $A_n$, associated with a sample;
    receiving, via the OCT system, a second complex-valued OCT A-scan, $A_{n+1}$, associated with the sample;
    determining a set of variance values for the first and second complex-valued OCT A-scans at different phases;
    determining a bulk motion phase shift, $\Delta\phi_B$, from the set of variance values;
    performing bulk motion compensation on the first and second complex-valued OCT A-scans using the bulk motion phase shift, $\Delta\phi_B$; and
    generating a flow image of the sample based on the bulk motion compensated first and second complex-valued OCT A-scans.

2. The method of claim 1, wherein determining a set of variance values for the respective first or second complex-valued OCT A-scans comprises determining respective variance values at $$\theta = 0, \frac{\pi}{2},$$

$\pi$, and $3\pi/2$ from a base phase, thereby generating the set of variance values $v_1$, $v_2$, $v_3$, and $v_4$.

3. The method of claim 2, wherein the bulk motion phase shift, $\Delta\phi_B$, is determined from the set of variance values $v_1$, $v_2$, $v_3$, and $v_4$ according to:

$$\Delta\phi_B = \operatorname{atan2}\left(\frac{v_3 - v_4}{v_2 - v_1}\right).$$

4. The method of claim 2, wherein individual variance values of the set of variance values are determined according to:

$$v = [\operatorname{std}(A_n - A_{n+1} \cdot \exp(-i \cdot \theta))]^2.$$

5. The method of claim 1, wherein the set of variance values is a first set of variance values, and wherein the method further comprises:
    determining multiple sets of variance values, including the first set, at different phase values spaced with reference to a base phase, wherein the base phase is different for each set of the multiple sets; and
    averaging the bulk motion phase shifts, $\Delta\phi_B$, determined from the respective sets of variance values to obtain an average bulk motion phase shift;

wherein the bulk motion compensation is performed on the complex-valued OCT A-scan using the average bulk motion phase shift.

6. The method of claim 1, wherein the bulk motion phase shift, $\Delta\phi_B$, is determined from the set of variance values according to:

$$v=C_1-C_2\cos(\Delta\phi_B+\theta).$$

7. The method of claim 1, wherein performing bulk motion compensation comprises calculating a third complex-valued OCT A-scan, $A_{new}$, according to the equation $$A_{new}=A_{n+1}\cdot\exp(i\cdot\Delta\phi_B).$$

8. The method of claim 7, further comprising correcting an OCT angiography A-scan, OCTA, according to:

$$OCTA=|A_n-A_{new}|.$$

9. The method of claim 7, further comprising correcting a Doppler OCT A-scan, doppler, by calculating $$doppler=angle(A_n \times conj(A_{new})).$$

10. A method comprising:
obtaining, via an optical coherence tomography (OCT) system, an OCT dataset associated with a sample, the OCT dataset including complex values;
determining multiple sets of variance values between A-scans of the OCT dataset, wherein individual sets of the multiple sets include variance values determined at different phases spaced relative to a base phase, and wherein the base phase is different for each individual set of the multiple sets;
determining a bulk motion phase shift for each individual set of variance values;
averaging the determined bulk motion phase shifts for the multiple sets to determine a bulk motion phase compensation;
compensating the OCT dataset based on the bulk motion phase compensation; and
generating a flow image of the sample based on the compensated OCT dataset.

11. The method of claim 10, wherein the different phases are evenly spaced from one another relative to the base phase.

12. The method of claim 11, wherein the individual sets of variance values include variance values $v_1$, $v_2$, $v_3$, and $v_4$, and wherein the bulk motion phase shift, $\Delta\phi_B$, for each individual set of variance values is determined according to:

$$\Delta\phi_B = \operatorname{atan2}\left(\frac{v_3-v_4}{v_2-v_1}\right).$$

13. The method of claim 10, wherein individual variance values of the sets of variance values are determined according to:

$$v=[std(A_n-A_{n+1}\cdot\exp(-i\cdot\theta))]^2;$$

wherein v is the individual variance value, $A_n$ is a first A-scan of the OCT dataset, $A_{n+1}$ is a second A-scan of the OCT dataset, and $\theta$ is the phase at which the individual variance value is determined.

14. The method of claim 10, wherein the OCT dataset is an OCT angiography dataset.

15. The method of claim 10, wherein the OCT dataset is a Doppler OCT dataset.

16. A system for bulk motion compensation in phased-based functional OCT imaging, the system comprising:

an OCT system configured to acquire a phased-based functional OCT dataset of a sample;
a logic subsystem; and
a data holding subsystem comprising machine-readable instructions stored thereon that are executable by the logic subsystem to:
receive, via the OCT system, a first complex-valued OCT A-scan, $A_n$, associated with a sample;
receive, via the OCT system, a second complex-valued OCT A-scan, $A_{n+1}$, associated with the sample;
calculate a set of variance values for the first and second complex-valued OCT A-scans according to:

$$v32\ [std(A_n-A_{n+1}\cdot\exp(-i\cdot\theta))]^2;$$

calculate a bulk motion phase shift, $\Delta\phi_B$, from the set of variance values;
perform bulk motion compensation on the first and second complex-valued OCT A-scans using the bulk motion phase shift, $\Delta\phi_B$; and
generate and display a flow image based on the bulk motion compensated first and second complex-valued OCT A-scans.

17. The system of claim 16, wherein to calculate the set of variance values, the logic subsystem is to calculate respective variance values at $$\theta = 0, \frac{\pi}{2},$$

$\pi$, $3\pi/2$ from a base phase to obtain respective variance values $v_1$, $v_2$, $v_3$, and $v_4$.

18. The system of claim 17, wherein the bulk motion phase shift, $\Delta\phi_B$, is calculated from the set of variance values according to:

$$\Delta\phi_B = \operatorname{atan2}\left(\frac{v_3-v_4}{v_2-v_1}\right).$$

19. The system of claim 16, wherein the set of variance values is a first set of variance values, and wherein the instructions are further executable by the logic subsystem to:
determine multiple sets of variance values, including the first set, at different phase values spaced with reference to a base phase, wherein the base phase is different for each set of the multiple sets; and
average the bulk motion phase shifts, $\Delta\phi_B$, determined from the respective sets of variance values to obtain an average bulk motion phase shift;
wherein the bulk motion compensation is performed on the complex-valued OCT A-scan using the average bulk motion phase shift.

20. The system of claim 16, wherein to perform the bulk motion compensation, the logic subsystem is to calculate a third complex-valued OCT A-scan, $A_{new}$, according to:

$$A_{new}=A_{n+1}\cdot\exp(i\cdot\Delta\phi_B).$$

21. The system of claim 20, wherein the instructions are further executable by the logic subsystem to correct an OCT angiography A-scan, OCTA, according to:

$$OCTA=|A_n-A_{new}|.$$

22. The system of claim 20, wherein the instructions are further executable by the logic subsystem to correct a Doppler OCT A-scan, doppler, according to:

$$doppler = angle(A_n \times conj(A_{new})).$$

* * * * *